United States Patent
Schraer et al.

(10) Patent No.: US 6,274,127 B1
(45) Date of Patent: Aug. 14, 2001

(54) ANHYDROUS ANTIPERSPIRANT COMPOSITIONS CONTAINING WATER-REACTIVE MONOMERS AS ANTIPERSPIRANT ACTIVE

(75) Inventors: Robert Michael Schraer, Fairfield, OH (US); Patricia Sue Raleigh, Highland Heights, KY (US); John Michael Gardlik, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/491,744

(22) Filed: Jan. 27, 2000

(51) Int. Cl.[7] .................. A61K 7/32; A61K 7/00
(52) U.S. Cl. .................. 424/65; 424/66; 424/67; 424/68; 424/400
(58) Field of Search .................. 424/65, 66, 67, 424/68, 400, 401, 78.02, 78.08

(56) References Cited

U.S. PATENT DOCUMENTS

| | | | |
|---|---|---|---|
| 4,508,705 | 4/1985 | Chaudhuri et al. | 424/47 |
| 4,650,670 | 3/1987 | Callingham et al. | 424/65 |
| 4,690,817 | 9/1987 | Davis et al. | 424/70 |
| 4,743,440 | 5/1988 | Callingham et al. | 424/46 |
| 4,822,596 | 4/1989 | Callingham et al. | 424/46 |
| 4,963,591 | 10/1990 | Fourman et al. | 514/944 |
| 5,372,804 | 12/1994 | Khoshdel et al. | 424/59 |
| 5,508,024 | 4/1996 | Tranner | 424/59 |
| 5,593,663 | 1/1997 | Leng et al. | 424/65 |
| 5,700,455 | 12/1997 | Hinterwaldner et al. | 424/70.14 |
| 5,869,600 | 2/1999 | Causton et al. | 528/422 |

*Primary Examiner*—Shelley A. Dodson
(74) *Attorney, Agent, or Firm*—William J. Winter

(57) ABSTRACT

Disclosed are non-adhesive antiperspirant compositions comprising a water or sweat-reactive monomer as the antiperspirant active, an anhydrous carrier, and an optional polymerization inhibitor, wherein the compositions are applied topically to the underarm or other suitable area of the skin to inhibit or prevent perspiration. The applied compositions form a discontinuous polymer-containing antiperspirant active on the applied skin surface, wherein the polymer-containing active is derived from water-reactive monomers that reacts with sweat at the opening of the sweat ducts after application, to thereby polymerize and form the polymer-containing antiperspirant active over and within the affected sweat ducts. The antiperspirant compositions and corresponding methods of application provide alternative antiperspirant active materials and product formulations, and provide improved efficacy and/or application cosmetics.

27 Claims, No Drawings

ANHYDROUS ANTIPERSPIRANT COMPOSITIONS CONTAINING WATER-REACTIVE MONOMERS AS ANTIPERSPIRANT ACTIVE

TECHNICAL FIELD

The present invention relates to antiperspirant compositions and corresponding methods of application, wherein the compositions comprise a new antiperspirant active in the form of water-reactive monomers.

BACKGROUND OF THE INVENTION

Many topical antiperspirant products are commercially available in a variety of formulations and product forms. These products typically contain a solid and/or liquid carrier in combination with an antiperspirant active such as an aluminum and/or zirconium salt. These aluminum and zirconium salts are used in almost every commercial antiperspirant product and have been used in this manner for decades.

Antiperspirant actives help to reduce or eliminate perspiration on the underarm or other areas of the skin. It is believed that these antiperspirant actives work by dissolving in sweat after application, diffusing as a dissolved material into the sweat ducts, and then precipitating in the sweat ducts to form a plug that then inhibits the flow of perspiration. It is believed that aluminum and zirconium salts work in this manner.

Today, commercially viable antiperspirant actives are limited mostly to the zirconium and aluminum salts. Other alternative actives have been investigated for antiperspirant efficacy over the years with very little practical success. Examples of such alternative actives include anticholinergics, antiadrenergics, aldehydes, and metabolic inhibitors such as oubain.

Still other alternative antiperspirant actives include water-insoluble, occlusive, film-forming polymers when applied topically to the skin. Examples of such antiperspirant polymers are described in U.S. Pat. No. 5,508,024, issued to Frank Tranner on Apr. 16, 1996. The application of these water-insoluble, polymeric films, however, often results in poor wash-off and application cosmetics. It has also been found that the application of these films does not always improve antiperspirant efficacy as compared to the application of commercially available antiperspirant products containing conventional zirconium and aluminum salts.

It has now been found that water-reactive monomers can be used as alternative antiperspirant actives to those actives currently available or otherwise known in the art. It has also been found that these water-reactive monomers can provide improved antiperspirant efficacy and/or cosmetics, especially when compared to the application of the antiperspirant polymers described hereinabove. These water-reactive monomers are formulated in an anhydrous base and applied topically to the underarm or other area of the skin. The topically applied monomers react with sweat and polymerize at the opening of the sweat ducts to form small polymeric plugs at the surfaces of the ducts, thus inhibiting or preventing the flow of perspiration from the affected ducts.

The topical application of water-reactive monomers has not previously been described in the context of antiperspirant products. These water-reactive monomers are, however, well known in the various arts for formulating topical adhesives and occlusive barrier films. Application of these formulations has been described primarily in the context of surgical wound adhesives, topically applied occlusive films and other similar applications.

It is therefore an object of the present invention to provide alternative antiperspirant compositions and antiperspirant actives to those which are currently available or otherwise known in the art. It is a further object of the present invention to provide such alternative compositions and antiperspirant actives through the use and application of water-reactive monomers contained by or within a suitable anhydrous carrier, and further to provide such alternative compositions and actives with improved antiperspirant efficacy and/or cosmetics.

SUMMARY OF THE INVENTION

The present invention is directed to antiperspirant compositions comprising novel antiperspirant active in the form of water-reactive monomers. These compositions preferably form discontinuous polymer-containing films on the skin, topically positioned over sweat ducts in the skin, wherein the polymer-containing films are derived from water-reactive monomers that react with sweat at the opening of the sweat ducts, to thereby polymerize and form the discontinuous polymer-containing films. The polymer-containing films over the sweat ducts act as plugs within the ducts to help prevent or inhibit the flow of perspiration from the affected sweat ducts. The present invention is also directed to methods for inhibiting or preventing perspiration by topically applying to the underarm or other appropriate area of skin a water-reactive monomer composition as described herein, which composition preferably comprises a water-reactive monomer, an anhydrous carrier, and a suitable polymerization inhibitor or other effective polymerization inhibition means.

It has been found that these topical antiperspirant compositions and applied methods of application provide alternative antiperspirant formulations and methods from those commercially available or otherwise known, without reliance upon traditional antiperspirant actives such as zirconium and aluminum salts. It has also been found that these compositions and applied methods provide improved antiperspirant efficacy and/or cosmetics as compared to many other more traditional antiperspirant products.

DETAILED DESCRIPTION OF THE INVENTION

The antiperspirant compositions of the present invention comprise water-reactive monomers, an anhydrous carrier, and preferably a suitable polymerization inhibitor or other effective polymerization inhibition means. These compositions are applied topically to the underarm or other appropriate area of the skin as a non-adhesive composition to inhibit or prevent perspiration.

The term "anhydrous" as used herein, unless otherwise specified, refers to those materials or compositions that are substantially free of added water. As it pertains to the compositions of the present invention, this means that the compositions are sufficiently free of added water such that the water-reactive monomers remain substantially unreacted or unpolymerized, e.g., less than about 50% reacted, prior to application. In this context, the term "anhydrous" can also mean that the composition contains water but that the water is isolated or otherwise prevented from reacting with the water-reactive monomer in the composition. The term "anhydrous" as used herein generally means that the material or composition preferably contains less than 1%, preferably less than 0.5%, most preferably zero percent, by weight of free or added water.

The term "non-adhesive" as used herein, unless otherwise specified, refers generally to the compositions of the present invention and the corresponding skin feel characteristics of those compositions when topically applied to the skin, wherein the compositions adhere to the applied surface of the skin but do not result in cosmetically noticeable adhesion of adjacent skin surfaces or clothing to the applied surface of the skin. These non-adhesive compositions are also preferably non-sticky after application.

The term "antiperspirant efficacy" as used herein, unless otherwise specified, refers to any incremental sweat reduction resulting from an antiperspirant composition as a result of the addition of the water-reactive monomer described herein. Sweat reduction is determined by the hot room procedure described in the Federal Register Volume 43, number 196 paragraph 350.43.

The term "water-reactive monomer" as used herein, unless otherwise specified, refers to those monomers or oligomers that react with water or sweat to polymerize under ambient conditions, or which otherwise react and polymerize during or after application to the underarm or other area of the skin. The term "water-reactive monomer" as used herein, unless otherwise specified, includes monomers and oligomers.

The term "ambient conditions" as used herein, refers to surrounding conditions at about one atmosphere of pressure (1 atm), at about 50% relative humidity, unless otherwise specified. All values, amounts and measurements described herein are obtained under ambient conditions unless otherwise specified.

The antiperspirant compositions and methods of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

The essential elements of the antiperspirant compositions of the present invention, including the essential elements of the corresponding methods of application, are described in greater detail hereinafter.

I. Water-reactive Monomers

The compositions of the present invention comprise a novel antiperspirant active in the form of water or sweat reactive monomers and/or oligomers (referred to collectively herein as "water-reactive monomers") in combination with a suitable anhydrous carrier, and preferably also in combination with a polymerization inhibitor or polymerization inhibition means. The concentration of the water-reactive monomer in the composition should be sufficient to provide the desired antiperspirant efficacy, when used alone or in combinations with other more conventional antiperspirant actives such as aluminum and/or zirconium salts, but will typically range from about 0.1% to about 60%, more typically from about 0.1% to about 30%, by weight of the composition.

The water-reactive monomers suitable for use in the compositions and methods of the present invention include any known or otherwise effective monomer or oligomer that when exposed to water rapidly polymerizes. Many such materials are known in the adhesive or formulation arts, and include those water-reactive monomers having an α-β unsaturated bond with at least one, e.g., one or two, electronegative moieties attached to the α carbon, preferably a water-reactive monomer having a cyano moiety, most preferably a cyanoacrylate ester in monomeric form that generally conforms to the formula:

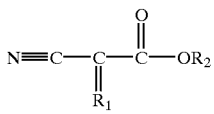

wherein $R_1$ and $R_2$ are independently selected from alkyl groups having from about 1 to about 18 carbon atoms, alkenyl groups having from about 2 to about 18 carbon atoms, cycloalkyl groups having from about 5 to about 8 carbon atoms, phenyl, 2-ethoxyethyl, 3-methoxybutyl, and substituents that conform to the formula:

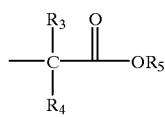

wherein $R_3$ and $R_4$ are independently selected from hydrogen and methyl; and $R_5$ is an alkyl group having from about 1 to about 6 carbon atoms, an alkenyl group having from about 2 to about 6 carbon atoms, an alkynyl group having from about 2 to about 6 carbon atoms, a cycloalkyl group having from about 3 to about 8 carbon atoms, benzyl, methyl benzyl, phenylethyl, phenyl, and phenyl substituted with from about 1 to about 3 substituents selected from hydroxy, chloro, bromo, nitro, alkyl group having from about 1 to about 4 carbon atoms and alkoxy groups having from about 1 to about 4 carbon atoms.

Preferred cyanoacrylate esters are those in which $R_1$ is methyl; $R_2$ is selected from n-butyl, isobutyl, t-butyl, 3-methoxybutyl, hexyl, octyl and decyl (preferably octyl); $R_3$ and $R_4$ are hydrogen; and $R_5$ is ethyl. Examples of preferred cyanoacrylate esters are octyl 2-cyanoacrylate, n-butyl 2-cyanoacrylate and combinations thereof.

II. Anhydrous Carrier

The compositions of the present invention comprise an anhydrous carrier suitable for topical application to the skin. Any such anhydrous carrier known or otherwise compatible with the other ingredients in the composition may be used. Concentration of the anhydrous carrier will vary with the selected formulation, ingredients, product form and so forth, but will generally range from about 1% to about 99%, more typically from about 20% to about 99%, even more typically from about 40% to about 95%, most typically from about 50% to about 95%, by weight of the composition.

The anhydrous carrier suitable for use in the composition may be in a solid, semi-solid or liquid form, but is preferably in liquid form. All such carriers must be compatible with the water-reactive monomer, or if not compatible then separated or otherwise isolated from the water-reactive monomer by a physical or chemical barrier, e.g., encapsulation, dual chamber packaging, polymerization inhibitors or inhibition means.

The anhydrous carrier is preferably substantially free of any substituent or material that would readily react with and trigger in situ polymerization of the water-reactive monomers. In general, any material that is a Lewis base is capable of triggering in situ polymerization of these water-reactive monomers, and are therefore preferably not formulated into the compositions herein. Non limiting examples of such reactive materials include free-water and amine-containing materials. In this context, the term substantially free means that the anhydrous carrier preferably contains less than the minimum amount of such reactive materials that would react with and trigger in situ polymerization of the water-reactive monomers.

The anhydrous compositions of the present invention, as well as the anhydrous carrier therein, may contain hydrated salts of organic acids, such as the optional zirconium and aluminum antiperspirant salts described herein, or other hydrated salts such as those described in U.S. Pat. No. 5,290,825, which description is incorporated herein by reference. It is believed that many of the hydrated salts can help reduce or prevent undesirable polymerization of the water-reactive monomers prior to topical application.

Non limiting examples of anhydrous carriers suitable for use in the compositions and methods of the present invention include straight and branched chain hydrocarbons having from about 8 to about 20 carbon atoms, mineral oils, organic esters, nonvolatile silicons such as dimethicone liquids, volatile or cyclic silicones such as cyclopentasiloxane, cyclohexasiloxanes, and combinations thereof.

The anhydrous carrier Preferably comprises a volatile carrier, more preferably a volatile silicone. These volatile silicones will typically have a viscosity as measured at 25° C. of less than about 10 centistokes (cs). They may be cyclic, linear or branched, non limiting examples of which are described in Todd et al., "Volatile Silicone Fluids for Cosmetics", Cosmetics and Toiletries, 91:27–32 (1976), which descriptions are incorporated herein by reference. It has been found that the water-reactive monomers do not as readily react and polymerize on the skin until after the applied anhydrous carrier evaporates from the topically applied composition. It is believed, therefore, that such reaction and polymerization is better controlled and/or optimized when the anhydrous carrier contains a volatile anhydrous carrier.

The volatile silicone carrier is preferably a cyclic silicone, more preferably a cyclic silicone having from about 3 to about 7, even more preferably from about 5 to about 6, silicon atoms. Most preferably are those volatile cyclic silicones which conform to the formula:

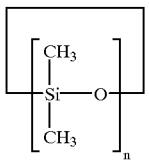

wherein n is from about 3 to about 7, preferably from about 5 to about 6, most preferably 5 (cyclopentasiloxane). Suitable volatile silicones for use herein include, but are not limited to, cyclopentasiloxane (commercially available from G. E. Silicones); Dow Coming 244 and Dow Corning 245 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

The anhydrous carrier may also include other polar or non-polar, volatile or nonvolatile, organic or non organic carriers known for use in antiperspirant/deodorant or other personal care product, or which are otherwise suitable for topical application to skin. Examples of such anhydrous carriers include those described in U.S. Pat. Nos. 5,750,096 (Guskey); 5,733,534 (Sawin et al.); 5,718,890 (Putman et al.); 5,429,816 (Hofrichter et al.); 5,605,681 (Trandai et al.); and 5,585,092 (Trandai et al.), which descriptions are incorporated herein by reference.

III. Polymerization Inhibitor

The compositions of the present invention may further comprise a polymerization inhibitor or other polymerization inhibition means to provide polymerization stability in the package and to control the rate of polymerization after the composition has been applied topically to the skin.

The polymerization inhibitor in the composition of the present invention can be any known or otherwise effective polymerization inhibitor or polymerization inhibition means suitable for use in or application with the anhydrous formulations described herein, provided that the polymerization inhibitor or polymerization inhibition means is also suitable for topical application to the skin and is otherwise compatible with the selected other ingredients in the composition.

Preferred polymerization inhibitors include anionic and free radical inhibitors when used in an effective amount to inhibit in situ polymerization of the water-reactive monomers prior to topical application. Any polymerization inhibitor can be used provided that it is also suitable for topical application to the skin and is otherwise compatible with the selected other ingredients in the composition. Concentration of the polymerization inhibitor typically ranges from about 10 ppm to about 10%, more typically from about 10 ppm to about 1% by weight of the composition.

Non limiting examples of suitable polymerization inhibitors include sulfur dioxide, nitric oxide, sulfonic acid, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxy anisole, butylated hydroxy toluene, t-butyl hydroquinone, alkyl sulfate, alkyl sulfite, 3-sulfolene, alkylsulfone, alkyl sulfoxide, mercaptan, alkyl sulfide, and combinations thereof. Polymerization inhibitors are also described in U.S. Pat. No. 3,527,224, which patent is incorporated herein by reference.

IV. Odor Controlling Active The compositions of the present invention preferably further comprise an odor controlling active, wherein the active can be any known or otherwise effective material for preventing, inhibiting, or otherwise masking product or perspiration malodors, provided that the odor controlling active is compatible with the other ingredients in the composition, including the water-reactive monomers. These odor controlling agents are well known in the deodorant and antiperspirant arts, and include deodorant actives, fragrances, deodorant perfumes, antiperspirant actives and combinations thereof.

The concentration of the optional odor controlling active should be sufficient to provide the desired odor controlling effect, but will generally range from about 0.05% to about 40%, more typically from about 0.5% to about 35%, even more typically from about 1% to about 30%, by weight of the composition. Concentrations will vary greatly depending upon the desired formulation and type of odor controlling agent selected.

Deodorant actives suitable for use in the composition are typically antimicrobial agents (e.g., bacteriocides, fungicides), malodor-absorbing materials, or combinations thereof. Preferred deodorant actives are antimicrobial agents, non-limiting examples of which include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4, 4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, famesol, phenoxyethanol, and combinations thereof. Most preferred among the antimicrobial agents are triclosan, triclocarban and combinations thereof.

Other deodorant actives suitable for use in the compositions herein include odor-absorbing materials such as carbonate and bicarbonate salts, including alkali metal carbonates and bicarbonates, ammonium and tetraalkylammonium.

Perfumes suitable for use in the compositions herein include any topical material that is known for or otherwise effective in masking malodor associated with perspiration, or which otherwise provides the composition with the desired fragrance. These include any perfume or perfume chemical, including pro-perfumes and deo-perfumes, suitable for topical application to the skin. The amount or concentration of the perfume should be effective to provide the desired fragrance or to otherwise help mask malodor, wherein the malodor is inherently associated with the composition itself or is associated with malodor development from perspiration.

Perfumes are made by those skilled in the art in a wide variety of fragrances and strengths. Typical perftimes and fragrances are described in Arctander, Perfume and Flavour Chemicals (Aroma Chemicals), Vol. I and II (1969); and Arctander, Perfume and Flavour Materials of Natural Origin (1960). U.S. Pat. Nos. 4,322,308 and 4,304,679, both incorporated herein by reference, disclose perfume or fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-anolide-1:4). Perfumes also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in perfumes herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable perfumes are those which mask or help to mask odors associated with perspiration (hereinafter referred to as odor masking perftumes), some non-limiting examples of which are described in U.S. Pat. Nos. 5,554, 588, 4,278,658, 5,501,805, and EP Patent Application 684 037 A1, all of which are incorporated herein by reference in their entirety. Preferred odor masking perfumes are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

Other odor controlling actives include those antiperspirant actives known or otherwise effective for providing antiperspirant efficacy when applied topically to the skin. These antiperspirant actives may be dissolved in the anhydrous carrier or otherwise dispersed throughout the composition as unsolubilized or partially unsolubilized solids.

The optional antiperspirant actives may be used at concentrations of from about 0.01% to about 40%, preferably from about 1% to about 30%, more preferably from about 5% to about 30%, by weight of the composition. These antiperspirant actives typically contain a substantial amount of bound water, although the weight percentages described hereinbefore are calculated on an anhydrous metal salt basis exclusive of bound water and any complexing agents such as glycine, glycine salts, or other complexing agents associated with the antiperspirant active.

Optional antiperspirant active suitable for use in the compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof Preferred aluminum salts for use in the composition include those which conform to the formula:

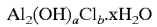

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Process for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the composition include those which conform to the formula:

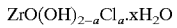

$$ZrO(OH)_{2-a}Cl_a \cdot xH_2O$$

wherein a is from about 1.1 to about 2.0; x is from about 1 to about 8; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued October 17, 1978, all of which are incorporated herein by reference.

V. Optional Suspending or Thickening Agent

The antiperspirant compositions of the present invention may further comprise a suspending or thickening agent to help provide the composition with the desired viscosity, rheology, texture and/or product hardness, or to otherwise help suspend any dispersed solids or liquids within the composition. The terms "suspending agent" and "thickening agent" are used interchangeably herein and include any material known or otherwise effective in providing suspending, gelling, viscosifying, solidifying or thickening properties to the composition or which otherwise provide structure to the final product form. These suspending or thickening agents include gelling agents, and polymeric or nonpolymeric or inorganic thickening or viscosifying agents. Such materials will most typically include organic solids, silicone solids, crystalline or other gellants, inorganic particulates such as clays or silicas, or combinations thereof.

The concentration and type of the optional suspending or thickening agent selected for use in the antiperspirant composition will vary depending upon the desired product form, viscosity, and hardness. For most suspending or thickening agents suitable for optional use herein, the concentration of such suspending or thickening agents will most typically range from about 0.1% to about 35%, more typically from about 0.1% to about 20%, by weight of the composition.

Preferred suspending or thickening agents include, for example, polycyanoacrylates, polylactic acid, polyglycolic acid, lactic-glycolic acid copolymers, polycaprolactone, lactic acid-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, copolymers of alkyl methacrylates and butadiene, silicone copolyols, silicone elastomers, copolymers of acrylates and siloxanes and combinations thereof.

Non limiting examples of suitable gelling agents include fatty acid gellants, salts of fatty acids, hydroxy acids, hydroxy acid gellants, esters and amides of fatty acid or hydroxy fatty acid gellants, cholesterolic materials, dibenzylidene alditols, lanolinolic materials, fatty alcohols, triglycerides, sucrose esters such SEFA behenate, inorganic materials such as clays or silicas, and other amide or polyamide gellants.

Still other examples of suitable gelling agents include fatty alcohols having from about 8 to about 40 carbon atoms, preferably from 8 to about 30 carbon atoms, more preferably from about 12 to about 18 carbon atoms. These gelling agents are wax-like materials which are most typically used at concentrations ranging from about 1% to about 25%, preferably from about 5% to about 20%, most preferably from about 10% to about 20%, by weight of the antiperspirant composition. Preferred are cetyl alcohol, myristyl alcohol, stearyl alcohol and combinations thereof, more preferably stearyl alcohol.

Other suitable gelling agents include waxes or wax-like materials having a melt point of above 65° C., more typically from about 65° C. to about 130° C., examples of which include, but are not limited to, waxes such as beeswax, carnauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792, Elsnau, issued Sep. 20, 1977, which description is incorporated herein by reference.

Other suitable gelling agents include fatty acid gellants such as fatty acid and hydroxy or alpha hydroxy fatty acids, having from about 10 to about 40 carbon atoms, and esters and amides of such gelling agents. Non-limiting examples such gelling agents include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof, and all other gelling agents which correspond to the following formula:

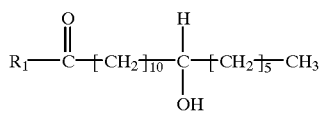

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, apartic acid, and combinations thereof. Other suitable amide gelling agents are described in U.S. Pat. No. 5,429,816, issued Jul. 4, 1995, and U.S. patent application Ser. No. 08/771,183, filed Dec. 20, 1996, which descriptions are incorporated herein by reference. Concentrations of all such gelling agents preferably range from about 0.1% to about 25%, preferably of from about 1% to about 15%, more preferably from about 1% to about 10%, by weight of the antiperspirant composition.

Non limiting examples of suitable triglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Other suitable suspending or thickening agents for use in the antiperspirant compositions include particulate suspending or thickening agents such as clays and colloidal pyrogenic silica pigments. Other known or otherwise effective particulate suspending or thickening agents can likewise be used in the antiperspirant composition. Concentrations of optional particulate thickening agents preferably range from about 0.1% to about 15%, more preferably from about 1% to about 15%, even more preferably from about 1% to about 8%, by weight of the composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75% by weight of the clay, more typically from about 40% to about 60% by weight of the clay.

Preferred thickening or gelling agents for the deodorant embodiments of the present invention are the salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate.

VI. Other Optional Materials

The composition of the present invention preferably further comprises a plasticizer suitable for topical application to the skin. Any plasticizer known or otherwise compatible with the other ingredients of the composition is suitable for use herein. The concentration of the plasticizer will vary with the selected composition and ingredients, but will typically range from about 0.1% to about 40%, more typically from about 1.0% to about 30%, by weight of the composition. The concentration should also be selected to minimize skin irritation resulting from the use of such materials.

Non limiting examples of suitable plasticizers include dimethyl sebacate, dioctyl sebacate, triethyl phosphate, tri (2-ethylhexyl) phosphate, tri (p-cresyl) phosphate, glyceryl triacetate, glyceryl tributyrate, diethyl sebacate, dioctyl adipate, isopropyl myristate, butyl stearate, lauric acid, dibutyl phthalate, trioctyl trimellitate, dioctyl glutarate, acetyl tri-n-butyl citrate, acetyl trihexyl titrate, butyl benzyl phthalate, dioctylphthalate, n-butyryl tri-n-hexyl citrate, diethylene glycol dibenzoate, combinations thereof, and similar other materials. Other examples of suitable plasticizers include those described in U.S. Pat. No. 2,784,127 and U.S. Pat. No. 4,444,933, which descriptions are incorporated herein by reference.

The compositions of the present invention may further comprise an adhesive modifier to reduce the adhesive characteristics of the composition to allow for more effective cosmetic application, more desirable skin feel after application, and improved wash-off. The concentration of such materials varies, but most typically ranges from about 1% to about 20%, by weight of the composition. Any material known for or otherwise effective in reducing the adhesive character of water-reactive monomers or other inherently adhesive material can be used. Non limiting examples of suitable adhesive modifiers include colloidal materials such as silica or alumina, and polymeric resins e.g., vinyl chloride/vinyl acetate and other synthetic resins as described in U.S. Pat. No. 4,444,933, which description is incorporated herein by reference, and other synthetic resins derived from monomeric materials such as itaconic acid, maleic acid, itaconic acid anhydrides, maleic acid anhydrides, and combinations thereof.

The antiperspirant compositions of the present invention may further comprise other optional materials known for use in antiperspirant, deodorant or other personal care product, or which are otherwise suitable for topical application to skin. Non limiting examples of such other optional materials include dyes or colorants, emulsifiers, distributing agents, pharmaceuticals or other topical actives, preservatives, surfactants, processing aides such as viscosity modifiers, wash-off aids, and so forth. Examples of such optional materials are described in U.S. Pat. No. 4,049,792, Elsnau, issued Sep. 20, 1977; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

It is understood that some of the optional materials described herein are physically or chemically incompatible with the water-reactive monomers also described herein, but that such ingredients can be formulated into the composition provided that the formulation contains a means to minimize or eliminate the incompatibility. Such means could include the use of physical or chemical barriers between incompatible materials in the composition, or the addition of other materials or means that otherwise minimizes or eliminates the incompatibility, non limiting examples of which are described in U.S. Pat. No. 5,290,825, which description is incorporated herein by reference VII. Product Form The antiperspirant compositions of the present invention can be formulated as any known or otherwise effective product form for providing topical application of antiperspirant or deodorant active to the desired area of the skin. Non limiting examples of such product forms include liquids (e.g., aerosols, pump sprays, roll-ons), solids (e.g., gel solids, wax solid sticks) and soft solids/creams/semi-solids, or lotions, and so forth. The antiperspirant compositions of the present invention are preferably liquids or semi-solids (e.g., soft solids, creams, semi-solids, lotions).

The antiperspirant products are generally stored in and dispensed from a suitable package or applicator device, such as a roll-on or cream dispenser with perforated application domes, etc. These packages should be sufficiently closed to prevent moisture, including atmospheric moisture, from contacting the composition and causing excessive in situ polymerization prior to application.

VIII. Method of Manufacture

The antiperspirant compositions of the present invention may be prepared by any known or otherwise effective technique, suitable for providing an anhydrous composition of the desired form and having the essential materials described herein. Many such techniques are described, for example, in the preparation of anhydrous cyanoacrylate adhesives and other product forms. Examples of such methods are described in U.S. Pat. Nos. 2,721,858; 3,254,111;

4,364,876; 3,995,641; and 3,554,990; which patents are incorporated herein by reference.

IX. Method of Use

The antiperspirant compositions of the present invention may be applied topically to the underarm or other suitable area of the skin in an amount effective to reduce or inhibit perspiration wetness. The composition is preferably applied in an amount ranging from about 0.1 gram to about 20 grams, more preferably from about 0.1 gram to about 10 grams, even more preferably from about 0.1 gram to about 1 gram, to each underarm or other desired area of the skin. The compositions are preferably applied to the underarm one or two times daily, preferably once daily, to achieve effective antiperspirant reduction or inhibition over an extended period.

The antiperspirant composition can also be applied every other day, or every third or fourth day, and then optionally to supplement application on off-days with other personal care products such as deodorants and/or conventional antiperspirant formulations.

The antiperspirant compositions are preferably applied to dry skin, wherein the applied composition on the skin is in the form of discontinuous polymer-containing films positioned over the sweat ducts in the skin, and/or otherwise forming plugs within the sweat ducts, wherein the resulting polymer-containing films/plugs are derived from water-reactive monomers that react with sweat or other aqueous liquid at the opening of the sweat ducts after application, to thereby polymerize and form discontinuous polymer-containing films over the sweat ducts and/or polymer-containing plugs within those sweat ducts.

X. Examples

The compositions described in Table 1 are examples of antiperspirant compositions of the present invention. In all cases, the polymerization inhibitors, e.g. butylated hydroxy anisole, sulfur dioxide and hydroquinone, are added during the manufacture of the cyanoacrylate monomer prior to formulation of the antiperspirant composition. All exemplified amounts are weight percentages based on the total weight of the antiperspirant composition, unless otherwise specified.

Composition Examples 1 through 4 are prepared as simple solutions at room temperature under an inert atmosphere such as nitrogen. In example 1, the dioctyl phthlate is dissolved in the n-butyl 2-cyanoacrylate then added to the cyclopentasiloxane under mild agitation. Examples 2 through 4 are prepared similarly. For example 5, cyclopentasiloxane, tribehenin, C 18-36 acid triglycerides, dimethicone and butyl stearate are added together then heated to 83° C. with mild agitation. The aluminum zirconium trichlorohydrex gly. is added. The mixture is cooled to 60° C. then sheared for 10 minutes with a high speed mixer such as those manufactured by Tecmar. The isohexyl 2-cyanoacrylate is added and the formula is cooled to 45° C. before pouring into a canister. The antiperspirant compositions described in Table 1 are applied topically to the underarm or other suitable area of the skin and form on the applied surface discontinuous polymer-containing films in contact topically positioned over sweat ducts in the skin, wherein the polymer-containing films are derived from water-reactive monomers reacting with sweat at the opening of the sweat ducts after application to the skin, to thereby polymerize and form the polymer-containing films over the sweat ducts and/or polymeic plugs within the sweat ducts. The applied compositions are non-adhesive and help to inhibit or prevent perspiration at the applied area of the skin.

What is claimed is:

1. A method for inhibiting or preventing perspiration, which method comprises the step of topically applying to skin a non-adhesive composition comprising a water-reactive monomer in an amount sufficient to provide antiperspirant efficacy.

2. The method of claim 1 wherein the non-adhesive composition is applied to an underarm area of the skin.

3. A method for inhibiting or preventing perspiration, which method comprises the step of topically applying to skin a non-adhesive composition comprising:
   a) from about 0.1% to 60% by weight of a water-reactive monomer;
   b) from about 1% to about 99% by weight of an anhydrous carrier; and
   c) a polymerization inhibitor;
   wherein the non-adhesive composition is applied to an underarm area of the skin.

4. The method of claim 3 wherein the water-reactive monomer contains an α-β unsaturated bond having at least one electronegative moiety attached to the a carbon.

5. The method of claim 4 wherein the water-reactive monomer contains a cyano moiety.

TABLE 1

Antiperspirant Compositions Containing Water-reactive Monomers

| Ingredient | Example 1 | Example 2 | Example 3 | Example 4 | Example 5 |
|---|---|---|---|---|---|
| cyclopentasiloxane | q.s. | q.s. | q.s. | q.s. | q.s. |
| n-butyl 2-cyanoacrylate | 12.00 | | | 5.00 | |
| isohexyl 2-cyanoacrylate | | 15.00 | | | 5.00 |
| n-octyl 2-cyanoacrylate | | | 20.00 | | |
| tribehenin | | | | | 5.00 |
| acrylatelvinylacetate copolymer | | | | 3.00 | |
| C18-36 Acid triglycerides | | | | | 1.25 |
| aluminum zirconium trichlorohydrex gly. | | | | | 5.00 |
| dimethicone | | | | | 5.00 |
| butylated hydroxy anisole | | .001 | .001 | .001 | .001 |
| hydroquinone | .001 | | | | |
| sulfur dioxide | .001 | .001 | .001 | .001 | .001 |
| dioctyl phthalate | 3.00 | | 7.5 | | |
| butyl stearate | | 5.25 | | 5.00 | 5.00 |
| perfume | | 1.0 | 1.0 | 1.0 | 1.0 |

6. The method of claim 5 wherein the water-reactive monomer is a cyanoacrylate ester that conforms to the formula:

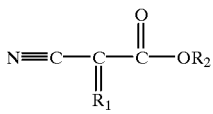

wherein $R_1$ and $R_2$ are independently selected from the group consisting of alkyl groups having from about 1 to about 18 carbon atoms, alkenyl groups having from about 2 to about 18 carbon atoms, cycloalkyl groups having from about 5 to about 8 carbon atoms, phenyl, 2-ethoxyethyl, 3-methoxybutyl, and substituents that conform to the formula:

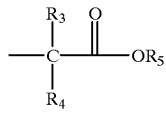

wherein $R_3$ and $R_4$ are independently selected from the group consisting of hydrogen and methyl; and $R_5$ is selected from the group consisting of an alkyl group having from about 1 to about 6 carbon atoms, an alkenyl group having from about 2 to about 6 carbon atoms, an alkynyl group having from about 2 to about 6 carbon atoms, a cycloalkyl group having from about 3 to about 8 carbon atoms, benzyl, methyl benzyl, phenylethyl, phenyl, and phen substituted groups with from about 1 to about 3 substituents selected from the group consisting of hydroxy, chloro, bromo, nitro, alkyl group having from about 1 to about 4 carbon atoms and alkoxy groups having from about 1 to about 4 carbon atoms.

7. The method of claim 6 wherein the cyanoacrylate ester is selected from the group consisting of octyl 2-cyanoacrylate, n-butyl 2-cyanoacrylate and combinations thereof.

8. The method of claim 5 wherein the non-adhesive composition further comprises from about 0.1% to about 40% by weight of a plasticizer.

9. The method of claim 8 wherein the non-adhesive composition comprises from about 1.0% to about 30% by weight of the plasticizer, and wherein the plasticizer is selected from the group consisting dimethyl sebacate, dioctyl sebacate, triethyl phosphate, tri(2-ethylhexyl) phosphate, tri(p-cresyl)phosphate, glyceryl triacetate, glyceryl tributyrate, diethyl sebacate, dioctyl adipate, isopropyl myrisate, butyl sterate, lauric acid, dibutyl phthalate, trioctyl trimelliate, dioctyl glutarate, acetyl tri-n-butyl citrate, acetyl trihexyl titrate, butyl benzyl phthalate, dioctylphthalate, n-butyryl tri-n-hexyl citrate, diethylene glycol dibenzoate, and combinations thereof.

10. The method of claim 2 wherein the non-adhesive composition further comprises from about 1% to about 20% by weight of an adhesive modifier.

11. A method for inhibiting or preventing perspiration, which method comprises the step of topically applying to skin a non-adhesive composition comprising a water-reactive monomer in an amount sufficient to provide antiperspirant efficacy and from about 1% to about 20% by weight of an adhesive modifier selected from the group consisting of silica, alumina, polymeric resins and combinations thereof;
wherein the non-adhesive composition is applied to an underarm area of the skin.

12. The method of claim 3 wherein the non-adhesive composition comprises from about 10 ppm to about 10% by weight of the polymerization inhibitor, and wherein the polymerization inhibitor is selected from the group consisting of sulfur dioxide, nitric oxide, sulfonic acid, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxy anisole, butylated hydroxy toluene, t-butyl hydroquinone, alkyl sulfate, alkyl sulfite, 3-sulfolene, alkylsulfone, alkyl sulfoxide, mercaptan, alkyl sulfide and combinations thereof.

13. The method of claim 2 wherein the non-adhesive composition further comprises an odor-controlling active selected from the group consisting of deodorant active, antiperspirant active, deodorant perfume, fragrance and combinations thereof, and wherein the anhydrous carrier represents from about 20% to about 95% by weight of the composition and contains a volatile silicone having a viscosity at 25° C. of less than about 10 centistokes.

14. The method of claim 13 wherein the antiperspirant active is selected from the group consisting of zirconium salts, aluminum salts and combinations thereof.

15. Anhydrous, non-adhesive, antiperspirant and deodorant compositions comprising:
a) from about 0.1% to 60% by weight of a water-reactive monomer,
b) from about 20% to about 99% by weight of an anhydrous carrier,
c) from 10 ppm to about 10% by weight of a polymerization inhibitor, and
d) from about 0.5% to about 35% by weight of an odor-controlling active selected from the group consisting of deodorant active, antiperspirant active, deodorant perfume and combinations thereof.

16. The composition of claim 15 wherein the water-reactive monomer contains an α-β unsaturated bond having at least one electronegative moiety attached to the a carbon.

17. The composition of claim 16 wherein the water-reactive monomer contains a cyano moiety.

18. The composition of claim 17 wherein the water reactive monomer is a cyanoacrylate ester that conforms to the formula:

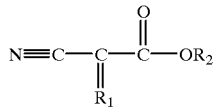

wherein $R_1$ and $R_2$ are independently selected from the group consisting of alkyl groups having from about 1 to about 18 carbon atoms, alkenyl groups having from about 2 to about 18 carbon atoms, cycloalkyl groups having from about 5 to 8 carbon atoms, phenyl, 2-ethoxyethyl, 3-methoxybutyl, and substituents that conform to the formula:

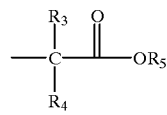

wherein $R_3$ and $R_4$ are independently selected from the group consisting of hydrogen and methyl; and $R_5$ is selected from the group consisting of an alkyl group having from about 1 to about 6 carbon atoms, an alkenyl group having from about 2 to about 6 carbon atoms, an alkynyl group having from about 2 to about 6 carbon atoms, a cycloalkyl group having from about 3 to about 8 carbon atoms, benzyl, methyl benzyl, phenylethyl, phenyl, and phen substituted groups with from about 1 to about 3 substituents selected from the group consisting of hydroxy, chloro, bromo, nitro, alkyl group having from about 1 to about 4 carbon atoms and alkoxy groups having from about 1 to about 4 carbon atoms.

19. The composition of claim 18 wherein the cyanoacrylate ester is selected from the group consisting of octyl 2-cyanoacrylate, n-butyl 2-cyanoacrylate and combinations thereof.

20. The composition of claim 15 wherein the composition further comprises from about 0.1% to about 40% by weight of a plasticizer.

21. The composition of claim 20 wherein the composition comprises from about 0.1% to about 30% by weight of the plasticizer, and wherein the plasticizer is selected from the group consisting dimethyl sebacate, diethyl sebacate, dioctyl sebacate, triethyl phosphate, tri(2-ethylhexyl)phosphate, tri (p-cresyl)phosphate, glyceryl triacetate, glyceryl tributyrate, dioctyl adipate, isopropyl myristate, butyl stearate, lauric acid, dibutyl phthalate, trioctyl trimellitate, dioctyl glutarate, acetyl tri-n-butyl citrate, acetyl trihexyl titrate, butyl benzyl phthalate, dioctylphthalate, n-butyryl tri-n-hexyl citrate, diethylene glycol dibenzoate, and combinations thereof.

22. The composition of claim 15 wherein the composition further comprises from about 1% to about 20% by weight of an adhesive modifier.

23. The composition of claim 22 wherein the adhesive modifier is selected from the group consisting of silica, alumina, polymeric resins and combinations thereof.

24. The composition of claim 15 wherein the composition comprises from about 10 ppm to about 10% by weight of the polymerization inhibitor, and wherein the polymerization inhibitor is selected from the group consisting of sulfur dioxide, nitric oxide, sulfonic acid, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxy anisole, butylated hydroxy toluene, t-butyl hydroquinone, alkyl sulfate, alkyl sulfite, 3-sulfolene, alkylsulfone, alkyl sulfoxide, mercaptan, alkyl sulfide and combinations thereof.

25. The composition of claim 15 wherein the antiperspirant active is selected from the group consisting of zirconium salts, aluminum salts, and combinations thereof.

26. The composition of claim 15 wherein the anhydrous carrier comprises a volatile carrier.

27. The composition of claim 26 wherein the volatile carrier is a cyclomethicone.

* * * * *

UNITED STATES PATENT AND TRADEMARK OFFICE
CERTIFICATE OF CORRECTION

PATENT NO.     : 6,274,127 B1
DATED          : August 14, 2001
INVENTOR(S)    : R. M. Schraer et al.

It is certified that error appears in the above-identified patent and that said Letters Patent is hereby corrected as shown below:

Column 4,
Line 33, "phenyl" should read -- phen --.

Column 5,
Line 25, "Preferably" should read -- preferably --.
Line 58, "Coming" should read -- Corning --.

Column 7,
Line 13, "famesol" should read -- farnesol --.
Line 34, "perftimes" should read -- perfumes --.

Column 8,
Line 3, "perftumes" should read -- perfumes --.
Line 49, "Process" should read -- Processes --.

Column 14,
Line 42, "a" should read -- α --.

Signed and Sealed this

Twenty-fifth Day of November, 2003

JAMES E. ROGAN
*Director of the United States Patent and Trademark Office*